United States Patent
Smith et al.

(10) Patent No.: US 6,607,716 B1
(45) Date of Patent: Aug. 19, 2003

(54) PEDICULICIDAL COMPOSITIONS, A KIT, AND METHODS OF USE

(75) Inventors: Robert Lee Smith, Albany, OR (US); Steven Dale Smith, Jefferson, OR (US); Wendy Dennis Langley, Albany, OR (US); John Mark Christensen, Corvallis, OR (US)

(73) Assignee: Tech Labs, Inc., Albany, OR (US)

( * ) Notice: Subject to any disclaimer, the term of this patent is extended or adjusted under 35 U.S.C. 154(b) by 42 days.

(21) Appl. No.: 09/817,706

(22) Filed: Mar. 26, 2001

Related U.S. Application Data

(63) Continuation-in-part of application No. 09/527,578, filed on Mar. 16, 2000, now abandoned, which is a continuation of application No. PCT/US99/22453, filed on Sep. 28, 1999.

(60) Provisional application No. 60/102,368, filed on Sep. 29, 1998.

(51) Int. Cl.$^7$ ............................. A61K 7/06; A61K 33/20
(52) U.S. Cl. ................ 424/70.1; 424/70.11; 424/70.22; 424/70.24; 424/70.31; 424/642; 424/670; 424/671; 424/679; 424/680; 424/681; 424/678
(58) Field of Search ........................... 424/70.1, 70.11, 424/70.22, 70.24, 70.31, 670, 671, 679, 680, 681, 678, 642; 514/880, 881, 944

(56) References Cited

U.S. PATENT DOCUMENTS

| | | | |
|---|---|---|---|
| 4,518,593 A | 5/1985 | Juvin et al. ................ 424/195 |
| 4,927,813 A | 5/1990 | Bernstein | |
| 4,940,579 A | 7/1990 | Randen ........................ 424/78 |
| 4,992,276 A | 2/1991 | Dills et al. .................. 424/439 |
| 5,053,222 A | 10/1991 | Takasu et al. ................. 424/7 |
| 5,227,163 A | 7/1993 | Eini et al. ................ 424/195.1 |
| 5,292,504 A | * 3/1994 | Cardin et al. ............... 424/405 |
| 5,411,992 A | 5/1995 | Eini et al. ................... 514/731 |
| 5,496,852 A | 3/1996 | Oliver ......................... 514/463 |
| 5,540,853 A | 7/1996 | Trinh et al. .................. 510/101 |
| 5,641,480 A | 6/1997 | Vermeer ................... 424/70.24 |
| 5,676,958 A | 10/1997 | Emerson et al. ....... 424/405.403 |
| 5,696,158 A | 12/1997 | Oliver ......................... 514/463 |
| 5,811,080 A | 9/1998 | Burgess et al. ................ 424/53 |
| 5,847,003 A | 12/1998 | Ptchelintsev et al. ........ 514/532 |
| 5,880,076 A | 3/1999 | Vermeer ...................... 510/123 |

FOREIGN PATENT DOCUMENTS

GB    2312620    1/1996

OTHER PUBLICATIONS

Arch Dermatol vol. 122, Mar. 1986, pp. 267–271, Meinking, et al.
Insects and Hygiene, , pp. 257–269, James R. Busvine.
Albany Democrat–Herald, Newspaper article, pp. 1–2a, Mar. 23, 1999.
Application Technology for Carbopol Resins and Cosmetic Formulations, BF Goodrich, TDS 60 Rev Jul. 1997.

* cited by examiner

Primary Examiner—Jyothsna Venkat
(74) Attorney, Agent, or Firm—Lori M. Friedman

(57) ABSTRACT

The invention discloses a natural treatment for ecto-parasitic infestation, particularly effective against lice be it head, body or pubic. A preferred gel composition includes a salt, a plant essence, and a pharmaceutically acceptable gelling agent. Besides gel, the composition designed for use on scalp hair may be formulated as a shampoo, a detangling spray conditioner, mousse, hair spray, or hair styling emulsion. The composition may be formulated as an ointment or lotion for topical use in areas with sparse hair. The invention also discloses a method of use of the composition, which is especially suited for treatment of the hair of infested children. The composition and method benefit from the soothing effects of aroma therapy. An additional benefit is that ecto-parasites do not develop resistance to the composition, which may be used repeatedly with no ill effects to the host.

12 Claims, 1 Drawing Sheet

PEDICULICIDAL COMPOSITIONS, A KIT, AND METHODS OF USE

RELATED PATENT APPLICATIONS

This is a United States continuation-in-part patent application based on patent application Ser. No. 09/527,578 filed on Mar. 16, 2000, now abandoned entitled "Pediculicide Compositions, a Kit, and Methods of Use", which is a continuation of PCT US99/22453 filed on Sep. 28, 1999 entitled "Pediculicide Compositions, a Kit, and Methods of Use", now abandoned which was based on U.S. provisional patent application Serial No. 60/102368 filed Sep. 29, 1998 entitled "Pesticidal Composition and Method of Use".

BACKGROUND OF THE INVENTION

Definitions Used in the Invention

Often times in this invention the term 'pediculicide' will be used to characterize the present invention, even though the pest that is targeted may be other than lice. The compositions are effective against lice, nits, and other ectoparasites such as bed bugs, fleas, aquatic leeches, scabies, mites, and the like.

In this invention the term 'nits' will mean both louse eggs, which are viable and alive, as well as egg casings without a live louse fetus inside. Live lice, eggs, and fetuses are all included as the pesticidal entities of this invention.

In this invention, 'natural' will mean that the pediculicidal compositions that are non-toxic. The product requires no label or other warning against its use by persons with certain allergies or medical conditions. Natural therapies are generally thought to require more time to achieve the therapeutic outcome than chemical cures. The examples and comparative examples recited herein indicate the treatment time difference between chemical (prior art) and natural (instant invention) therapies for pediculosis.

In this invention, 'Pharmaceutically acceptable gelling agent' will mean a material that thickens the composition sufficiently to remain on the hair of a scalp for an extended period of time. The material is thick enough not to drip; run or leak out from under the plastic cap provided as part of the instant kit which provides the tools necessary for at least one application to treat lice-infested scalp hair. The viscosity of the gel is an important feature of this invention. The gel composition is thick enough to immobilize the ecto-parasite so that the active ingredients can kill them. A range of thickness required may be expressed as a viscosity ranging from about 3,000 to about 15,000 centipoise (cps). A more preferred viscosity range for the gel composition of the instant invention is from about 6,000 to about 14,000 cps. A still more preferred range is from about 10,000 to about 12,000 cps. It should be noted that the terms 'viscosity increasing agent' and 'thickener' are synonymous and are used interchangeably in this patent application.

In this invention, 'stable' will mean that the composition will not decompose either chemically or physically. This is especially important for the gel compositions of this invention that are part of a kit sold to consumers for treating lice-infested scalp hair. The shelf life of the gel in said kit is at least three years.

In this invention, there are two different categories of fragrance components optionally included in the pediculicidal compositions. One category will impart a soothing fragrance to the composition. This category of fragrance may be from any source. A preferred category of fragrance used in the compositions of this invention will be derived from a plant, and called a plant essence. Another, more preferred category of fragrance will be a plant essence that has pediculicidal activity as well as a pleasant aroma.

Another important definition of this invention is what is meant by 'areas without hair'. In this invention, 'areas without hair' will mean body parts such as limbs which may have body hair but do not have the concentration of hair as does the scalp or the pubic area. It is on these body parts that the active composition of the invention will be formulated as an ointment or a lotion.

Background Discussion

Infestation of lice (pediculosis), fleas and similar ectoparasites is a common problem. Infestation is often spread from shared hats, combs, lockers, closets, and other unavoidable contacts in school. Infestation can easily spread to other children, or family members by touching or via shared clothing or hair accessories. According to the National Pediculosis Association, there are reportedly 10–12 million cases of pediculosis reported annually.

Head lice (*pediculus humanus capitis*) are small parasitic insects that have adapted to living on the scalp and neck of a host organism. Long associated with human hosts, lice are usually acquired by children in school settings, as has been described previously. Head lice derive nutrients by blood-feeding several times per day. They cannot survive for more than a day at room temperature without ready access to, the host's blood. A nymphal louse hatches from its egg after about eight days of development, and begins to feed, grow and develop until it attains the adult stage 2–3 weeks after hatching Body lice are closely related to head lice, but are less frequently encountered in the United States. Body lice generally infest body hair but may migrate to the scalp and facial hair. They usually remain on clothing near the skin and deposit their eggs near the seams of garments. Body lice are usually acquired through direct contact with an infested person or their clothing.

Pubic or crab lice are found in the pubic hair and are usually not associated with children. Public lice are generally transmitted through sexual contact. They may also spread through sharing a bed with an infested person.

Once present on the head, the average female louse has a lifespan of about 25 days and lays up to 10 eggs (nits) each day. The nits attach to the hair shaft by a strong adhesive. The nits hatch within 7–9 days producing more adult lice which continue the cycle. As the lice feed, they cause intense skin irritation. Scratching may lead to secondary infections of the scalp.

In the past, various chemical agents and insecticides have been used to treat pediculosis. These compounds include DDT, hexachlorocyclohexane (HCH), malathion, lindane, cholinesterase inhibitors, pyrethrins, permethrin, and the like. Many of these chemical insecticides have toxic and other unpleasant side effects.

Besides toxicity, another problem with using chemical insecticides to control ecto-parasites such as head lice is that the pests may develop resistance to the insecticides. According to Busvine in his work *Insects and Hygiene*, recent years have seen the emergence of lice which are resistant to DDT and HCH in Britain, Denmark, France, Hungary, Canada, and the United States.

In the past, attempts have been made to eradicate this pest. For example, in U.S. Pat. No. 4,927,813, Bernstein uses a therapeutically effective amount of formic acid in a pharmaceutically acceptable carrier. The procedure recited therein requires application of a formic acid-based material that will dissolve the cement that hold nits in the hair, maintaining the solution on the hair for certain time periods, and washing with shampoo following the treatment. This method may be unduly long, laborious, and difficult to follow, especially if the lice-infested person is young and uncomfortable. Another danger of this art is that formic acid is believed to be toxic. Its absorption through the skin may effect the liver.

Another example of an insecticidal shampoo composition used to treat pediculosis is cited by Juvin et al in U.S. Pat. No. 4,518,593. Juvin et al disclose a shampoo comprising a non-ionic wetting agent, acetic acid, and a plant extract. Examples recited therein use multiple washings. The remedy proposed by Juvin et al is in the form of shampoo.

Plant extracts are mentioned in U.S. Pat. No. 5,676,958 to Emerson et al. This art discloses the use of aromatic aldehydes to kill undesirable parasites. The active insecticidal moiety in Emerson is also formulated into a shampoo.

U.S. Pat. No. 5,696,158 to Oliver discloses a composition that uses piperonal dissolved in water and various alcohol solvents that repel lice and have a pleasant fragrance. U.S. Pat. No. 5,496,852 also to Oliver discloses a method of repelling lice using piperonal-based formulations.

Fragrance is also noted in U.S. Pat. Nos. 5,227,163 and 5,411,992 to Eini et al. These documents disclose the use of various terpenes as lice repellents. Pleasant fragrance is a concern of both these patents. Both Oliver and Eini comment about unpleasant smells associated with many pesticidal louse repellents.

An attempt was made in the past to utilize salt compositions for treating lice. One such instance is found in British patent application GB 2,312,620 A. Disclosed herein is a composition for the treatment of hair containing parasitic insects comprising flour, sodium chloride, and water. The color and opacity of this solution are not mentioned, nor is its ease of use.

SUMMARY OF THE INVENTION

The present invention discloses compositions useful in combating certain ecto-parasite insect pests. These compositions are particularly useful against parasite infestations on host organisms, and are particularly effective against head, body, or pubic lice as well as against other troublesome ecto parasites in humans. The invention further includes a kit containing a gel composition of this invention and methods for its use.

The invention has several features, no single one of which is solely responsible for its desirable attributes. Without limiting the scope of the invention, as expressed by the claims that follow, its more prominent features will now be discussed briefly. After considering this discussion, and particularly after reading the section entitled "Detailed Description of the Preferred Embodiments", the reader will understand how the features of the invention provide its benefits. The gel compositions of the invention are non-toxic and easy to use to effectively control various ecto-parasites on the scalps of host organisms. Furthermore, many of the compositions provide a soothing aroma during use. Another benefit of the invention is a kit containing all that-is needed to apply the composition to the scalp of someone suffering from pediculosis.

Being natural, the compositions of this invention require no adverse health warnings and may be used by pregnant women and others with sensitivity to chemical pediculicides. The compositions are safe and easy to use. They are sold as over-the-counter (OTC) preparations. No special label warnings are required for the instant compositions in the United States. An example of a special label warning is that required for the use of pyrethrins. Pyrethrins are present in other OTC pediculicides, and is contraindicated in those allergic to ragweed.

An added benefit of its safety to host organisms of ecto-parasites is that the ecto-parasites do not develop resistance to the composition. Developed resistance to chemical pesticides is a cause of 'super bugs' which can survive the pesticides applied to eradicate them.

In addition to its natural, non-chemical nature, another important feature of this invention is that its pediculicidal compositions are available in several forms. The forms include gels, shampoos, detangling spray conditioners for use on hair of the host organisms. Other hair preparations that may be formulated include hair mousse, hair spray, hair styling emulsion, and the like.

As will be shown in the Examples that follow, the active ingredients of the instant pediculicidal composition may be formulated into a wide variety of products. The various products will have in their formulations ingredients appropriate to their use. For example, a shampoo will have foaming agents.

If the ecto-parasite infestation is present in areas without dense amounts of hair, such as the scalp, compositions of the instant invention may be formulated as an ointment or a lotion. The safety and natural quality of these compositions are maintained.

The invention also features a kit. The kit is sold as an over the counter product. The kit is designed so that the pediculicidal composition includes a pleasant fragrance and is applied by an adult in a home setting without the need for medical intervention if the lice-infested person is a child. In this manner, the soothing aroma of the pediculicidal gel composition helps make treatment pleasant and effective while keeping both the child and caregiver comfortable. The kit includes a gel whose composition is active against ecto-parasitic infestation of the hair, a fine toothed comb used to remove dead parasites and parasite eggs from the hair shafts, and a plastic cap to cover the hair while the gel is in contact with the infested area to insure that the gel applied to the hair stays moist and warm for the duration of the treatment. Instructions for the use of the kit are printed right on the box in which the kit is packaged. After initial use of the gel in the kit, it is recommended that another application takes place 7–10 days after the first treatment to kill any newly hatched lice.

Another important feature of the invention is that the pediculicidal gel composition may be formulated with varying degrees of translucency. The gel may be a creamy white gel, a translucent gel, or a clear gel. Each gel allows for visual inspection of scalp hair for live lice, nymphs and nits. Such visual inspection is important, especially if the lice-infested person is a child and the caregiver seeks reassurance that the hair is free of lice.

In each gel formulation, the nits and lice can be seen for inspection and removal. This is because 1) if the gel applied is clear or translucent, the lice and nits can be seen through the hair and gel by light transmission. 2) if the gel applied to the hair is opaque, it is white. The lice and nits are dark in color, and can be seen because of the contrast between the dark lice and the white gel. Some users have found that if the hair to be treated is light in color, such as blond, gel that is opaque facilitates inspection and removal of lice remains. The opacity or clarity of the gel is immaterial to its effectiveness; the active pediculicidal ingredients are present in each formulation. The translucency or opacity of the gel depends on the amount of oil used in the formulation and will be described in more detail shortly.

The Gel Pediculicidal Compositions

The gel composition of this invention comprises water, a salt present in an amount effective to kill ecto-parasites, a gelling agent that increases the viscosity of the composition, a gel promoter, and an optional plant essence that is a pediculicide. The gel composition has a viscosity ranging from 3,000 to 15,000 cps. A more preferred viscosity range for the gel composition of the instant invention is from about 6,000 to about 14,000 cps. A still more preferred range is from about 10,000 to about 12,000 cps.

In the instant invention a salt is an active ingredient present in an amount effective to kill ecto-parasites. This effective amount of salt in a gel composition may contain from about 1 to about 50 weight percent of at least one ionic salt. A preferred amount of salt, or combination of salts present in the composition of the instant invention may range from about 5 to about 20 percent by weight. An even more preferred amount is 10 percent by weight.

The salt ingredient of the instant invention comprises at least one metallic anion and one non-metallic cation. Preferred salts are at least one salt selected from the group consisting of sodium chloride, potassium chloride, magnesium chloride, potassium iodide, sodium iodide, potassium iodide, zinc acetate, and calcium chloride. An especially preferred salt is sodium chloride.

Gelling agents used in preparing the gel compositions of this invention may be selected from a wide variety of known and available pharmaceutically acceptable materials. The gelling agents are typically present in an amount from 0.5 to 30 percent by weight. A preferred amount of gelling agent may range from about 0.5 to 15 weight percent. A still more preferred about is from about 0.5 to 5 percent by weight.

Preferred gelling agents may be selected from the group consisting of acacia, alginic acid, bentonite, calcium carboxymethylcellulose, sodium carboxymethylcellulose, microcrystalline cellulose, powdered cellulose, cellulose acetate phthalate, methyl isopropyl chitosan, sodium croscarmellose, crospovidone, ethyl cellulose, guar gum, hydroxyethyl cellulose, hydroxypropylmethyl cellulose, hydroxypropyl cellulose, hydroxymethyl cellulose phthalate, methylcellulose, poloxamer, polymethylacylates, polyvinyl alcohol, polyvinyl pyrolidone, propylene glycol alginate, sodium alginate, sodium starch glycolate, pregelatinized starch, and xanthan gum.

Of these, preferred gelling agents may be selected from the group consisting of, hydroxyethyl cellulose, carboxyvinyl polymer (sold as Carbomer® by Union Carbide or Carbopol® by BF Goodrich), hydroxypropylmethyl cellulose, hydroxypropyl cellulose, hydroxymethyl cellulose phthalate. The most preferred gelling agent used in this invention is Carbopol®.

When Carbopol® is used, the manufacturer, BF Goodrich, suggests that a pH from 2.5 to 10 is necessary for satisfactory gelling. In this invention, when Carbopol® is used as the gelling agent, a neutralizing agent is added to raise the pH to about 5.5 to about 8 so that gelling occurs.

In the gel composition of this invention, a gel promoter is also used. The gel promoters are substances that interact with the gelling agent by increasing viscosity and stabilizing the gel. Gel promoters in this invention maybe selected from the group consisting of cocoamide diethanol amine (DEA), vanilla, and glycerol monostearate. These materials are believed to hydrogen bond to more than one site of the gelling agent molecule. It is known that gels that contain oil have a tendency to be unstable. In this invention, various gel compositions are formulated that are stable. It is thought that anything that has the ability to hydrogen bond to multiple sites of the gelling agent will serve this purpose.

There is may be at least one plant essence in any of the compositions of this invention that is a pediculicide. Typically, it is present from about 0.01 to about 10 percent by weight. These plant essences may be derived from a plant or synthetic. Some are oils and some are not. Certain plant essences have pediculicidal activity. Some are antiseptic as well. Pediculicidal plant essences are used in the instant invention to synergistically improve the pediculicidal activity of the composition. If present, they also add a pleasant aroma to the composition. This is important in aroma therapy and emphasizes the soothing nature of the product.

The pediculicidal plant essences used in the pediculicidal composition of this invention may be selected from the group consisting of essence of cinnamon bark, cinnamon leaf, eucalyptus, tea tree oil, camphor, geranium, neem, lemongrass, azalea, anise oil, lavender, garlic, birch tar oil, citronella, sabadilla, oregano, mezereum, staphysagria, ledum palustre, ledum latifolium (JACQ), sage, and habanera.

An unusual and surprising feature of the gel compositions of the present invention is its clarity. It has been discovered that the gel may be clear, translucent, or opaque depending on the amount of oil(s) used in the formulation. Specifically, if the amount of oil used in the formulation is minimal, the resulting gel will be clear or slightly translucent. If the amount of oil used is 0.5 weight percent or higher, the formulated gel composition will be an opaque white material. Specific examples of these opacity differences will be presented in the formulae that follow.

Another unusual and unexpected feature of this invention is that applicants have successfully employed Carbopol to successfully thicken the salt active ingredient of the instant gel formulation. The gel, as contained in the instant kit, has a viscosity over 10,000 cps. As can be seen in the gel formulations that follow, a 2.25:10 ratio of salt::Carbopol would be expected to have a much lower viscosity than 10,000 cps. In fact, it would be expected to have a viscosity of less than about 3,000 cps, according, to the BF Goodrich literature on Carbopol. Accordingly, applicants ability to raise the viscosity nearly four times higher and formulate a stable gel is considerably remarkable and unpredicted. It is also surprising that such a gel is chemically and physically stable for extended periods of time.

Several gel compositions have been formulated with combinations of the various of the ingredients listed above. These gel compositions are formulated to be applied topically to the scalp of a lice-infested person.

One preferred gel composition of the instant invention comprises:

from 10 to 20 weight percent of a salt;
from 0.5 to 30 weight percent of a gelling agent;
from 1 to 5 weight percent of a surfactant;
from 0.1 to 30 weight percent of a gel promoter;
from 0.3 to 5 weight percent of a neutralizing agent;
from 0.01 to about 10 weight percent of at least one plant essence that is a pediculicide, and the balance water.

A preferred gelling agent is a carboxyvinyl polymer and a preferred salt is sodium chloride. If the plant essence used in the formulation is an oil that is present in at least 0.5 weight percent, this formulation will be opaque. If the fragrance used in the formulation is anise oil, a fragrance fixative such as benzyl benzoate may also be employed. A preferred amount of benzyl benzoate is at least about 2.5 weight percent.

Another preferred gel composition comprises:

about 10 weight percent sodium chloride salt;

about 2.25 weight percent of a carboxyvinyl polymer gelling agent;

about 0.5 weight percent of anise oil plant essence;

about 4 weight percent of a combination of the performance additives cocoamide diethanolamine, 2-amino-2-methyl-1-propanol, benzyl benzoate, and the remainder purified water. This formulation will be opaque, since the anise oil plant essence is present in 0.5 weight percent.

A series of preferred gel formulations will be described in detail shorty. These gel compositions contain at least one salt, a gelling agent, a variety of performance additives selected from the group consisting of neutralizing agents, surfactants, and co-surfactants. The preferred gels may optionally contain at least one fragrance, which fragrance may be a plant essence that has pediculicidal activity as well as a pleasant aroma.

Ointment Composition

This invention also includes an ointment. The ointment composition of this invention has a viscosity of from 2,500 to 1,000,000 cps and comprising water, a salt present in an amount effective to kill ecto-parasites, a gelling agent, a gel promoter, a plant essence that is a pediculicide, and a thickener. More specifically, it comprises from 10 to 20 weight percent of the salt, from 0.5 to 30 weight percent of the gelling agent, from 0.1 to 3 weight percent of the gel promoter, from 0.5 to 5 weight percent of the plant essence, and from 5 to 15 weight percent of the thickener. Preferably, the thickener is stearic acid.

Lotion Composition

This invention also includes a lotion. The lotion composition of this invention has a viscosity of from 100 to 10,000 cps and comprises water, a salt present in an amount effective to kill ecto-parasites, a gelling agent, a gel promoter, and a plant essence that is a pediculicide. More specifically, the lotion comprises from 10 to 20 weight percent of the salt, from 0.5 to 30 weight percent of the gelling agent, from 0.1 to 3 weight percent of the gel promoter, from 0.5 to 5 weight percent of the plant essence.

Shampoo Composition

This invention also includes a shampoo. The shampoo composition of this invention has a viscosity of from 350 to 15,000 cps and comprises water, a salt present in an amount effective to kill ecto-parasites, a plant essence that is a pediculicide, and a surfactant. More specifically, the shampoo comprises from 10 to 20 weight percent of the salt, from 0.5 to 5 weight percent of the plant essence, and from 2 to 45 weight percent of the surfactant. Preferably, the salt is selected from the group consisting of sodium chloride, potassium chloride, magnesium chloride, potassium iodide, sodium iodide, potassium iodide, zinc acetate, and calcium chloride. It may include a conditioner, a foaming agent, a viscosity agent, a chelating agent, a preservative, and a humectant, a fragrance, and a fragrance fixative.

One preferred shampoo composition comprises:

a) about 10 weight percent of the salt;

b) about 12 weight percent of the surfactant;

c) about 1 weight percent of the conditioner;

d) about 10 weight percent each of the foaming agent and the viscosity agent;

e) up to about 1 weight percent each of the chelating agent and the preservative;

f) about 10 weight percent of the humectant;

g) up to about 1 weight percent of the fragrance;

h) about 2 weight percent of the fragrance fixative; and the remainder purified water.

Detangling Spray Conditioner

This invention also includes a detangling spray conditioner for hair. The detangling spray conditioner of this invention has a viscosity of from 100 to 1,000 cps and comprises water, a salt present in an amount effective to kill ecto-parasites, a plant essence that is a pediculicide, a conditioner, and a surfactant. More specifically, the conditioner comprises from 10 to 20 weight percent of the salt, from 0.5 to 5 weight percent of the plant essence, from 0.5 to 5 weight percent of the conditioner, and from 0.5 to 10 weight percent of the surfactant. The preferred salt is selected from the group consisting of sodium chloride, potassium chloride, magnesium chloride, potassium iodide, sodium iodide, potassium iodide, zinc acetate, and calcium chloride.

One preferred detangling spray conditioner comprises:

about 10 weight percent of the salt;

about 10 weight percent of the conditioner;

up to about 1 weight percent of a humectant;

up to about 1 weight percent of a preservative;

up to about 1 weight percent of a fragrance; and about 80 percent purified water.

General

All the pediculicidal compositions of the present invention contain at least one ionic salt. In simplest terms, the salts of interest in the instant invention comprise at least one metallic cation and at least one non-metallic anion. These salts may be used individually or in combination. The non-metal portion of the salt is at least one non-metal selected from the group consisting of halides, sulfates, phosphates, selenates, acetates, citrates, succinates, formates, or nitrates. Preferred non-metals include halides, sulfates, and nitrates. A most preferred non-metal is chloride. The metallic portion of the salt may be generally classified as alkali metals or alkali earth metals. The elements include the metals listed in Groups IA and IIA, respectively, of THE PERIODIC TABLE OF THE ELEMENTS. The metals of particular interest include at least one of the metals from the group consisting of potassium, sodium, magnesium, tin, calcium, selenium, zinc, aluminum, iron, cesium or manganese. Preferred salts of the composition of this invention are chlorides, nitrates or sulfates of the Groups IA and IIA metals. Preferred metals may be selected from the group consisting of sodium, potassium, calcium, zinc, and magnesium.

The instant composition contains from about 1 to about 30 weight percent of at least one ionic salt comprising at least one metallic anion and one non-metallic cation listed supra. Preferred salts may be at least one salt selected from the group consisting of sodium chloride, potassium chloride, magnesium chloride, potassium iodide, sodium iodide, potassium iodide, zinc acetate, and calcium chloride. An especially preferred salt is sodium chloride.

A preferred amount of salt, or combination of salts present in the composition of the instant invention may range from about 5 to about 15 percent by weight. An even more preferred amount is about 10 percent by weight.

Besides salt, any of the compositions may include a fragrance. For example, the fragrance may be a plant essence selected from the group consisting of chamomile, lemon peel oil, chaparral, parsley seed, aloe vera, jasmine, lavender, sage, gum benzoin, calendula, oregano, carrot seed, vanilla, cinnamon bark oil, cinnamon leaf, eucalyptus oil, tea tree oil, camphor, geranium, neem, lemongrass, azalea, anise oil, lavender, garlic, birch tar oil, citronella, sabadilla, mezereum, staphysagria, ledum palustre, ledum latifolium (JACQ), sage, cedarwood, and habanera.

When used in a formulation of the present invention, a preferred plant essence is fragrant, pediculicidal, and antiseptic. Included in this category are lavender, eucalyptus, tea tree oil, and geranium. Sage, gum benzoin, calendula, and carrot seed are antiseptic. The antiseptic property is quite desirable when treating lice infestation in children. The itching caused by the lice oftentimes leads to scratching. Scratching, especially in children, can lead to breaking of the skin and bleeding. Antiseptics may help in controlling infection in these cases.

The most preferred plant essences may be selected from the group consisting of essence of cinnamon bark oil, anise oil, lavender, eucalyptus oil, and lemon peel oil. The pediculicidal plant essence in the instant composition may be present from about 0.01 to about 2 weight percent. A preferred amount of the plant essence used for fragrance may range from about 0.2 to 0.5 weight percent.

The compositions of the present invention that are formulated with at least one of the above-listed plant essences provide a natural pediculicide against live host organisms which provides soothing effects of aroma therapy when combined with at least one salt, a gelling agent, and a various performance additives in an aqueous medium. The natural formulation is made of ingredients that do not require adverse health warnings and may be used by pregnant women, by those allergic to ragweed and people with sensitivity to chemical pediculicides.

In the case of vanilla, it has been surprisingly discovered that vanillin not only imparts a pleasant fragrance to the composition, but acts as a thickener. When used in the instant composition, a small amount (0.1 of 1%) of sodium metabisulfite is also added to the formulation. (See Example 2 of this patent application for details of this formulation).

The most preferred plant essences may be selected from the group consisting of essence of cinnamon bark oil, anise oil, lavender, eucalyptus oil, and lemon peel oil. The pediculicidal plant essence in the instant composition may be present from about 0.01 to about 2 weight percent. A preferred amount of the plant essence used for fragrance may range from about 0.2 to 0.5 weight percent. The compositions of the instant invention may have both types of plant essences. If present, the pleasant aroma of the plant essence is serendipitous and provides the aroma therapy that is also a benefit on this invention.

Another possible ingredient compositions of the present invention is a fragrance fixative. A fragrance fixative helps stabilize the added fragrance. Possible fragrance fixatives for the instant composition may be selected from the group consisting of coconut oil, benzyl benzoate 2.5 weight percent, benzyl benzoate 1.0 weight percent, and soybean oil. The preferred fragrance fixative in the present invention is benzyl benzoate. The preferred amount of benzyl benzoate is at least about 2.5 weight percent in the compositions of this invention, although it may be present in as much as 30 weight percent.

Other ingredients of the composition of the present invention include performance additives. The performance additive component(s) of this invention may be one or more performance additives selected from the group consisting of a surfactant, a detergent, an emulsifier, a dispersant, a foaming agent, a conditioner, a chelating agent, a preservative, a foam booster, a stabilizer, a viscosity agent, a humectant, an antioxidant, a neutralizing agent, a cosurfactant, a skin emollient, and an insect repellent. Since the instant composition may be formulated as a gel, shampoo, conditioner, ointment, or lotion the type and amount of performance additive(s) used will vary according to the requirements of each formulation.

Depending on their role in the composition, these performance additives are generally present in the formulation in an amount from about 0.1 to about 30 weight percent. A more preferred amount of performance additive ranges from about 0.1 to about 10 weight percent. An even more preferred amount of performance additive ranges from about 0.1 to 5 weight percent. The performance additives given in Tables 5–8 in the Examples that follow present them in specific roles and amounts.

Specific performance additives used as surfactants in this invention include poly(oxyethylene sorbitan monolaurate) (polysorbate 20), polysorbate 80, sorbitan monolaurate (Span 20™ ICI; Arlacel™, Croda), sodium laurel sulfate, or coocoamidopropylbetaine. These surfactants enable the composition to easily foam in water.

A more inclusive list of performance additives includes conditioners such as erucamidopropyl diammonium chloride, hydrolyzed collagen, hydrolyzed protein, babassuamidopropalkonium chloride; viscosity agent, foam stabilizer, or co-surfactant such as cocoamide DEA; emollients such as coconut oil, soybean oil, or wheat germ oil; humectants such as propylene glycol or glycerol, stabilizers such as dimethicone copolyol, calcium disodium ethylene diamine tetraacetic acid; preservatives such as one or more alkyl parabens, benzethonium chloride; and antioxidants such as sodium metabisulfite. When Carbolpol® is used as a gelling agent, a neutralizing agent is heeded to raise the pH to a neutral value of between 5.5 and 8. In this invention, neutralizing agents may be selected from the group consisting of 2-amino-2-methyl-1-propanol (AMP 95™), sodium hydroxide, or triethanol amine, Chelating agents are used in the gel composition to keep them from degrading when exposed to light. Various chelating agents are used In this invention; a typical chelating used in this invention is disodium ethylenediaminetetraacetic acid (EDTA). The chelating agent keeps metal ions such as iron, calcium and other multi-valent metal ions from clouding the gel. The gel may cloud when exposed to UV light.

A preferred neutralizing agent is selected from the group consisting of 2-amino-2-methyl-1-propanol (AMP 95™), sodium hydroxide, and triethanolamine. A more preferred neutralizing agent is 2-amino-2-methyl-1-propanol (AMP 95™)

Method

This invention also includes a method for eradicating an ecto-parasitic population in the hair of host organisms. It comprises contacting the infested area with a composition comprising water, a salt present in an amount effective to kill ecto-parasites, a gelling agent that increases the viscosity of the composition, a gel promoter, and a plant essence that is a pediculicide. The gel applied to hair may be translucent to allow visual inspection of ecto-parasites in the hair after application of the gel and subsequently inspecting the hair.

The gel may also be formulated into an opaque, thick white gel. Whether the gel is opaque or clear depends on various formulation parameters. More specifically, the amount and type of oils used in the formulation determines the opacity of the gel. The clarity or opacity of the gel depends upon the types and amounts of oils that are used in formulating a pediculicidal gel of the present invention.

For example, the gel formulation of example 1 contains 0.53 weight percent lavender and anise oils, and it is opaque. If the amount of oil in the formulation is ,equal to or less than 0.25 weight percent of the total, the gel is clear If the oil concentration is equal to or greater than 0.5 weight percent, the gel made from it will be opaque. Lastly, if the amount of oil is between 0.25 and 0.50 weight percent of the total weight of the composition, the gel will be translucent. The differing degrees of clarity or opacity of the gels of this invention are a continuous progression of totally clear (no oils whatsoever) to totally opaque white gel (at an oil concentration of at least 0.5 percent.

In any case, the nits and lice can be seen for inspection and removal. This is because 1) if the gel applied is translucent, the lice and nits can be seen through the hair and gel by light transmission, or 2) If the gel applied to the hair is opaque, it is white. The lice and nits are darker in color than the opaque white gel, and can be seen because of the contrast between the dark lice and the white gel.

To eradicate lice and other ecto-parasites from a lice-infested head, a gel of the present invention is applied to the ecto-parasitic infested area and allowed to remain in contact with the hair for at least 30 minutes. After this time has elapsed, the hair is combed to remove the ecto-parasites and the composition is rinsed off with water. The gel composition is reapplied as needed to remove ecto-parasites without harm to the host organism.

Instead of a gel, the pediculicide composition applied to the infested hair may be in the form of a shampoo or detangling spray conditioner. The ecto-parasite population to be controlled by a composition of this invention are selected from the group consisting of head lice, body lice, bed bugs, fleas, aquatic leeches, scabies, and mites.

Kit

This invention also includes a kit. This kit includes at least one bottle of a natural pediculicidal gel composition discussed above active against ecto-parasitic infestation;
  a fine toothed comb used to remove dead parasites and parasite eggs from the hair shafts; and
  at least one plastic cap to cover the hair while the gel is in contact with the infested area to insure that the gel applied to the hair stays moist and warm for the duration of the treatment.

The gel is not messy, in that it does not run or drip from the hair when applied and used as directed in the kit. The material is pleasant to use. The plant essence contained in the gel of the kit has aroma-therapeutic properties, is non-irritating, and may have antiseptic properties. When formulated as a gel for the kit, the composition is packaged in an opaque, plastic squeeze bottle. The material is viscous but will flow smoothly from the bottle when pressed. The bottle is plastic to prevent breakage and opaque to protect against light and prolong shelf stability.

DETAILED DESCRIPTIONS OF THE PREFERRED EMBODIMENTS

The preferred embodiment of the kit of this invention, illustrating all its features, will now be discussed in detail. This embodiment depicts the kit of this invention as shown in the accompanying drawing, which is for illustrative purposes only. The drawing includes the following figures, with like numerals indicating like parts:

The Kit

Figure 1:
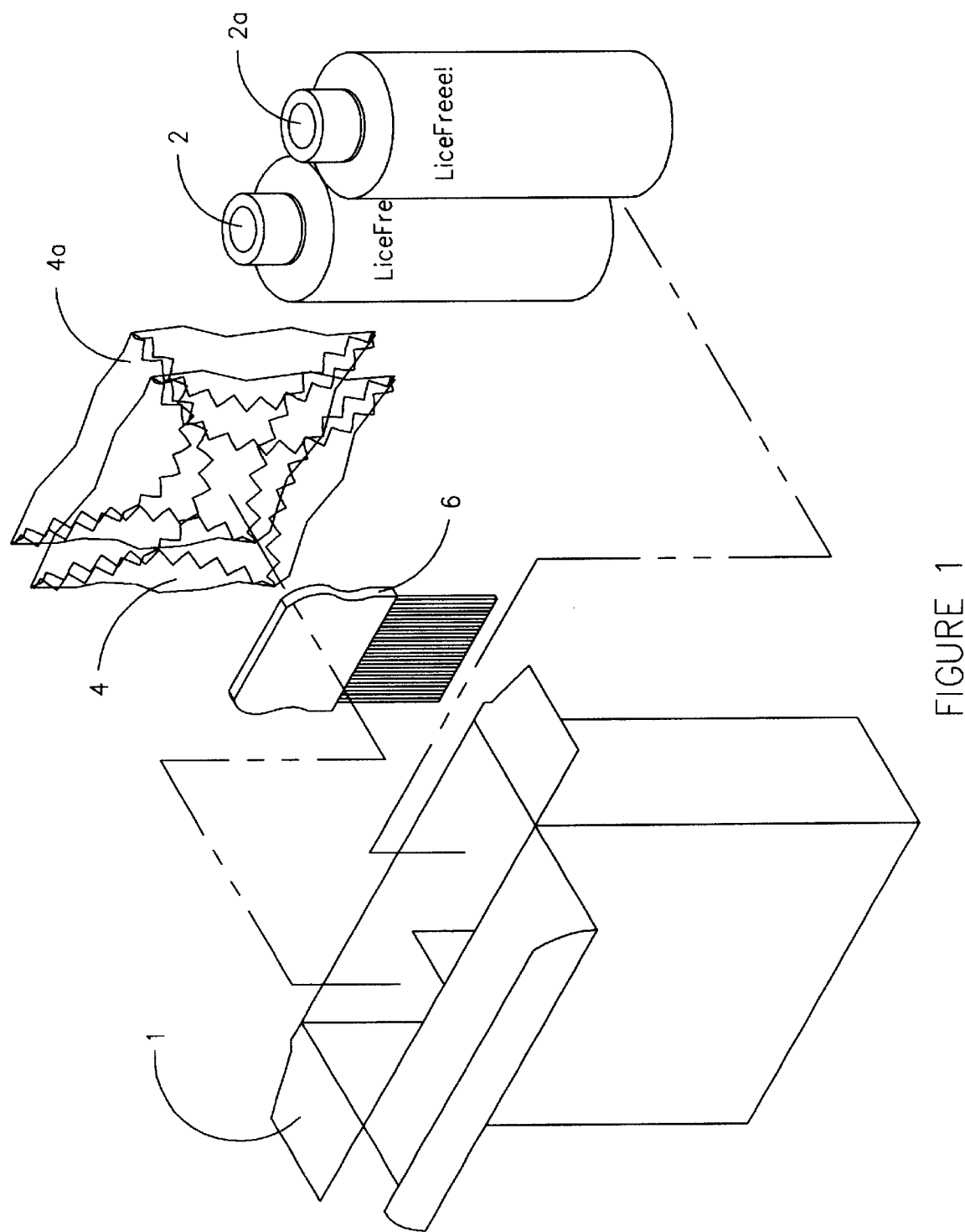
FIG. 1 is an exploded perspective view of the kit of this invention.

The invention is best understood by reference to FIG. 1 that depicts the kit 1 of this invention. The kit 1 is used by a person who is him or herself infested with lice or, in many cases, by a parent or other adult who treats lice-infested child.

The kit 1 contains the materials needed for at least one application of pediculicidal gel to a lice-infested head of hair. Instructions for home use of the kit 1 are printed on the outside of the box 1a which holds the items included in the kit 1. As shown in FIG. 1, the kit 1 includes one or two four-ounce bottles 2 and 2a of the a pediculicidal gel composition of the invention. Said composition is labeled "LiceFreee!®" and is sold by Tec Laboratories Inc., Albany, Oreg. In this invention, future references to this composition will be made using the abbreviation "LF"

The kit 1 further contains a fine toothed comb 6 that is made by Health Enterprises, North Attleboro, Mass. This comb, or an equivalent device, is to be used to remove dead lice and nits from the hair.

Additionally the kit 1 contains two plastic caps 4 and 4a. Use of a plastic cap on the infested area insures that the product applied to the hair stays moist and warm for the duration of the treatment.

Although the examples that follow are mainly concerned with head lice, the compositions, kit and method of this invention are expected to be efficient in ridding a plurality of ecto-parasites from live hosts.

EXAMPLES

The following examples 1–9 depict both factory and laboratory procedures that enable the present invention. There are also examples that demonstrate the efficacy of the present invention and compare it to other products, describe a method for its use, and describe the use of the instant kit. A list of what each example covers follows below:
  Example 1 is a factory procedure for a LiceFreee!® Pediculicide Gel.
  Example 1A is a manufacturing procedure for pediculicidal lotion.
  Example 1B is a manufacturing procedure for a pediculicidal ointment.
  Example 2 is another factory procedure for a LiceFreee!® Pediculicide Gel.
  Example 3 depicts a method of use for the pediculicidal kit of this invention.
  Example 4 is a laboratory comparison of the efficacy of the Pediculicide of the present invention to treatment with water.

Example 5 is laboratory comparison of Lice Freee!® to another commercially-available pediculicide as an ovicide.

Example 6, 7, and 7Ai–v are laboratory preparations of a variety of pediculicidal gels.

Example 8 is a laboratory preparation of a pediculicidal detangling spray conditioner for lice-infested scalp hair.

Example 9:is a laboratory preparation of a pediculicidal shampoo.

Example 1

Factory Production of LiceFreee!® Pediculicide Gel

The pediculicidal composition of this invention is made and packaged in a manufacturing environment. The following procedure is used for manufacturing of a composition of this invention:

| Ingredient | wt. In lbs. | wt % | Purpose |
|---|---|---|---|
| Purified water, USP | 2153.00 | 79.50 | vehicle |
| Sodium chloride, USP (Morton Salt Co.) | 270.80 | 10 | active ingredient |
| Carbopol Ultrez 10 ® (Dow) | 60.95 | 2.25 | gelling agent |
| 2-Amino-2-methyl-1-propanol AMP 95 ™, (Angus Chemical) | 60.95 | 2.25 | neutralizing agent |
| Benzyl benzoate (Morflex, Inc) | 66.90 | 2.47 | fragrance fixative |
| Lavender (Bell Flavors & Fragrances) | 0.80 | 0.03 | active, fragrance |
| Anise oil (Berje) | 13.55 | 0.50 | active, fragrance |
| Polysorbate 20 (VWR, Inc). | 54.15 | 2.00 | surfactant |
| Cocoamide DEA Ninol 40 CET ™ (Stepan Chemical) | 27.10 | 1.00 | viscosity increasing agent, co-surfactant |

Manufacturing Procedure for Pediculicide Gel of Example 1

The above ingredients (except water) are weighed into clean buckets or beakers. They are then covered, affixed with an "in-process" label, and dispensed to a manufacturing area for further processing.

To start formulation, purified water is added, the mixer is turned on and the speed turned up until a vortex is formed just above the disperser blade (about 34 Hz).

Carbopol® gelling agent is then added to the mixer. Any Carpobol® sticking to the sides of the mixer are scraped off the sides of the mixer with a large spatula and added to the rest of the ingredients. The mixing is continued until the Carbopol® is dispersed and no undissolved solids remain. Dissolving time is about ten minutes.

Sodium chloride or other salt is added and mixed until dissolved. The mixing is continued until no chunks of solids are present in the bottom of the mixer. AMP 95™ or other neutralizing agent is added. The mixer speed is then adjusted until a vortex is formed just above the disperser blade. Anise oil and lavender (or other plant essence(s)) and polysorbate 20 (or other surfactant) are then added. Ninol is added and the mixer speed adjusted so that the vortex remains just above the disperser blade (about 3440 Hz.)

The weight of the tank is noted and recorded. The mixer speed is adjusted until a vortex forms just above the disperser blade (about 56 Hz). The mixture is recirculated and mixed at full speed for at least 30 minutes and as long as 2 hours.

After the mixing procedure is complete, recirculation is stopped. The mixer speed is reduced to about 10–15 Hz. The mixing/recirculation time is recorded. A sample of at least 100 ml is retrieved from the tank valve or product transfer pump. The sample is tested in the factory for quality control. After sampling is determined to be satisfactory, the lid of the formulation tank is closed. The bottling process then begins.

In this invention, "mixing" will mean applying a mixing blade to the composition which rotates the material from side to side. "Recirculation" means that a pump on the bottom of the tank lifts the composition from bottom to top of the tank. Therefore, recirculation means there is both side to side and top to bottom exchange of materials.

Example 1A

Manufacturing Procedure for Pediculicidal Lotion

To formulate the active ingredients of Example 1 into a lotion, for topical treatment to eradicate ecto-parasites from areas other than the scalp by modification of the ingredients of Example 1. More specifically, the amount of gelling agent and neutralizing agent will be reduced and a skin emollient and surfactant will be added.

A suitable lotion is made from the following ingredients:

| Ingredient | wt. In lbs. | Purpose |
|---|---|---|
| Carbopol ® | 27.09 | thickener |
| AMP-95 ™ | 27.09 | neutralizing agent |
| Isopropyl Myristate | 27.09 | skin emollient |
| Sorbitan monolaurate Span 20 | 27.09 | surfactant |

The other ingredients of Example 1 remain the same. A lotion may also be formulated by the ingredients of Example 1 omitting the neutralizing agent AMP 95™.

Example 1B

Manufacturing Procedure for Pediculicidal Ointment

To make an ointment, the gel formula of Example 1 is adjusted by adding a natural lubricant and thickener such as stearic acid (270.8 pounds, or 10 weight percent) and reducing the water content to 270.80 pounds, or 10 weight percent. The ointment is mixed at 65 degrees Celsius and allowed to cool overnight

Example 2

Another Factory Production of LiceFreee!® Pediculicide Gel

In a manner similar to Example 1, the following ingredients were combined in a manufacturing environment to form a pediculicidal composition.

| Ingredient | wt. In lbs. | wt % | Purpose |
|---|---|---|---|
| Purified water, USP | 2249.00 | 83.05 | vehicle |
| Vanillin (VWR, Inc.) | 27.05 | 1.00 | fragrance, thickener |
| Carbopol Uttrez 10 ® (BF Goodrich) | 60.95 | 2.25 | gelling agent |
| Sodium chloride, USP (Morton Salt Co.) | 270.80 | 10.00 | active ingredient |
| 2-Amino-2-methyl-1-propanol AMP 95 ™, (Angus Chemical) | 59.60 | 2.20 | neutralizing agent |
| Anise oil (Berje) | 13.55 | 0.50 | active, fragrance |
| Polysorbate 20 ™ (VWR, Inc.) | 27.10 | 1.00 | surfactant |
| Sodium Metabisulfite American International Chemical (AIC) | 1.00 | 0.0003 | stabilizer |

In a manner similar to Example 1, the ingredients listed above were weighed and measured in a manufacturing facility. Vanillin, present as a fragrance and thickener in Example 2, necessitates the addition of sodium metabisulfite as a stabilizer. The sodium metabisulfite is stirred in and mixed until it is thoroughly dispersed. It is added to the mixer after rest of the ingredients have been combined.

Quality control sampling and packaging procedures are carried out in a manner similar to that of Example 1.

Example 3

Method of Use of the Pediculicidal Kit of This Invention

The gel formulation produced by Example 1 or Example 2 are bottled and packaged into a kit. The kit is purchased as an over-the-counter preparation in variety stores, drug stores, health food stores, grocery stores, and mass merchandise outlets. The formulations of the instant invention that are in a form other than gel (lotion, ointment, shampoo, detangling spray conditioner) are used in the same way that other such products in common use are used and require no special procedures.

Procedure for removing head lice using the kit: Head lice live on the scalp and lay small white eggs (nits) on the hair shaft close to the scalp. Nits are most easily found on the nape of the neck or behind the ears. All personal headgear, scarves, clothing contacting the head, and bed linen should be laundered in hot water and dried using the hot cycle of the dryer for at least 20 minutes. Items that cannot be machine washed should be dry cleaned followed by sealing in plastic for at least two weeks. Comb and other hair tools used by a lice-infested person should be disinfected by soaking in very hot water (temperature above 130° F.) for at least five minutes. Thorough vacuuming of floor in all rooms inhabited by infested persons is recommended.

To use the materials of the kit the following procedure should be followed. If the lice-infested person is a child, the procedure should be conducted by a parent or other responsible adult. Instructions for use are printed on the box 1A which contains the materials that comprise the kit of this invention.

The user is instructed to shake one of the bottles 2 or 2a that are supplied in the kit. The hair of the lice-infested person is not to be wet or washed before using the gel composition supplied in at least one bottle of the kit. The contents of said bottle is applied to the dry hair and entire scalp of a lice-infested person until both hair and scalp are entirely wet with contents of one or both bottles. The amount of material needed for thorough coverage will depend on the length and amount of hair to be treated. Any remaining material should be kept in the bottle, resealed, and stored at room temperature.

After thorough application of the gel contained in at least one bottle to hair, one of the plastic caps 4 or 4a should be opened and put on the head on top of the gel-coated hair. The cap should remain on the head for at least an hour. For best results, the lice-infested person should stay indoors in a room whose temperature should range from about 59 to about 77 degrees F.

After an hour has elapsed, the cap is removed from the head. With the pediculicidal gel still in the hair, all dead lice and nits are removed by combing with the comb 6 that is supplied with the kit for this purpose. The comb 6 is then rinsed under running water.

After all lice and nits are removed from hair and scalp, the hair is rinsed with warm, running water. The comb 6 should then be thoroughly inspected, and when it is clean, hair should be combed a second time to insure complete removal of all ecto-parasites A second treatment with a pediculicidal gel of this invention is recommended 7–10 days after the first treatment to kill any newly hatched lice. The product may be reused as often as necessary without the fear of the ecto-parasites developing resistance to the pediculicidal gel of the present invention.

Example 4

Laboratory Comparison of the Efficacy of the Instant Pediculicide to Treatment With Water The protocol followed in this comparison was based on published procedures used to assess ovicidal activity and 'killing' time of the head louse as written by (Meinking et al., 1986). For this particular test, only killing times of nymph and adult lice were carried out.

Lice were collected from the heads of ten volunteers from the Albany, Oreg., area. Hair was combed with a louse comb and the collected lice were placed in Petri dishes. The test area was kept at a warm ambient temperature (27–30° C.). Routine spraying of storage and test areas was prohibited. Within 2 hours, the lice were placed on the forearm of a volunteer and allowed to feed to repletion. Tests were then initiated.

Three tests were carried but, each consisting of a sample and a control. For each, 34 lice, containing both nymphs and adults, were placed in a Petri dish lined with terrycloth and covered with purified water or the instant composition (LF gel). For the latter, the lice were covered with a thin layer of gel such that each louse was immersed in the material but still visible, for a period of one hour. Lice were monitored for peristalsis at five-minute intervals for the first hour and then every 30 minutes.

All lice treated with LF gel stopped moving within a half hour, while the average survival time of lice treated with water was approximately a half day. All three treatments were consistent; results follow in Table 1.

TABLE 1

(for Example 4)

| Sample | No. of lice | Period of time to last movement |
|---|---|---|
| Experiment 1 | | |
| Lice Freee! ® | 34 | 25 minutes (m) |
| Water | 34 | 18 hours (h) 12 m |
| Experiment 2 | | |
| Lice Freee! ® | 34 | 23 m |
| Water | 34 | 16 h 45 m |
| Experiment 3 | | |
| Lice Freee! ® | 34 | 16 m |
| Water | 34 | 14 h 45 m |

Example 5

Comparison of Lice Freee!® to Another Commercially-available Pediculicide as an Ovicide This example compares the pediculicidal efficacy of Lice-Freee!® with another commercially available pediculicide. For this example, compositions with 1% permethrin as the active ingredient were used. Example of commercially available pediculicides that contain 1% Permethrin are well known, for example, Nix® or Rid®. For Example 5, the control group was treated with water. The comparison was based on ASTM E1517-93.

In this example, nits treated with Lice Freee!® were immersed for 60 minutes. Nits treated with 1% Permethrin compositions were immersed for 10 minutes. Control replicates were immersed in water for 60 minutes.

Label instructions for the commercially available pediculicides containing 1% permethrin indicate a 10 minute exposure time. Label instructions for Lice Freee!® indicate a 60 minute exposure time. Sixty minutes was chosen for Lice Freee!® as a practical and safe length of time to insure maximum saturation time of the product to the infested area. Sixty minutes was also the amount of time that the control samples were treated with water.

The difference in treatment times of the two pediculicides is in accordance with the previously noted distinction between natural (instant invention) and chemical (prior art) pediculicides. Although the natural treatment time is longer than the chemical treatment time, the instant composition requires no label warnings. The permethrin-containing product label warns against use by pregnant women and that the product may cause breathing difficulty or asthma in susceptible persons In Examples 5A, 5B, and 5C whose testing results are given in Tables 2, 3, and 4 respectively, two enhancements to the ASTM test method were made. The first was the use of five replicates used for the treatments and the control. The second was the use of tap water instead of distilled water. The results of Examples 5A–5C are tabulated and presented below.

TABLE 2

(Example 5A)
Testing Results: Human Body Louse Nits
Example 5A: Control: water   Immersion Time: 60 minutes

| | | | Unhatched* | | | |
|---|---|---|---|---|---|---|
| No | Total | Hatched | Early Stage | Late Stage | Emergent Stage | |
| 1 | 30 | 27 | 2 | 0 | 1 | |
| 2 | 30 | 24 | 2 | 3 | 1 | |
| 3 | 29 | 29 | 0 | 0 | 0 | |
| 4 | 30 | 27 | 0 | 1 | 2 | |
| 5 | 28 | 24 | 0 | 3 | 1 | |
| | 147 | 131 | 4 | 7 | 5 | TOTALS |

TABLE 3

(Example 5B)
Testing Results: Human Body Louse Nits
Example 5B: LiceFreee! ®   Immersion Time: 60 minutes

| | | | Unhatched* | | | |
|---|---|---|---|---|---|---|
| No | Total | Hatched | Early Stage | Late Stage | Emergent Stage | |
| 1 | 28 | 0 | 0 | 28 | 0 | |
| 2 | 30 | 0 | 0 | 30 | 0 | |
| 3 | 27 | 0 | 0 | 27 | 0 | |
| 4 | 29 | 0 | 0 | 29 | 0 | |
| 5 | 29 | 0 | 0 | 29 | 0 | |
| | 143 | 0 | 0 | 140 | 0 | TOTALS |

TABLE 4

(Example 5C)
Testing Results: Human Body Louse Nits
Example 5C: 1% permethrin   Immersion Time: 10 minutes

| | | | Unhatched* | | | |
|---|---|---|---|---|---|---|
| No | Total | Hatched | Early Stage | Late Stage | Emergent Stage | |
| 1 | 29 | 0 | 0 | 27 | 2 | |
| 2 | 29 | 0 | 0 | 29 | 0 | |
| 3 | 30 | 0 | 0 | 29 | 1 | |
| 4 | 30 | 0 | 0 | 30 | 0 | |
| 5 | 30 | 0 | 0 | 30 | 0 | |
| | 148 | 0 | 0 | 145 | 3 | TOTALS |

Definitions for Testing Results Tables 2–4
  Early Stage: no visible differentiation of embryo
  Late Stage: eye spots and/or limbs visible through chorion
  Emergent Stage: fully formed nymphs in process of emerging but not yet separate from egg.

Examples 6–9

Laboratory Formulation of Various Pediculicidal Hair Products

As has been stated, the pediculicidal composition of the instant invention may be formulated and applied in other forms than the gels manufactured in Examples 1 and 2. The gels that are prepared in Examples 6 and 7 use different ingredients than those used in Examples 1 and 2.

Specifically, the gel of Example 6 uses a soothing emollient, a different viscosity increasing agent, and a different fragrance. Example 7 uses a different gelling agent. Neither Examples 6 nor 7 use vanillin or sodium metabisulfite stabilizer.

Examples 8 and 9, each with a table of ingredients, disclose the ingredients and formulae for a shampoo and a detangling spray conditioner. The amounts of ingredients and procedures are scaled to laboratory (not manufacturing) quantities.

Example 6

Laboratory Preparation of a Pediculicidal Gel

A pediculicidal gel was prepared in the laboratory using the ingredients listed below. The quantities, in grams, are smaller than the commercially manufactured gels of Examples 1 and 2.

| Ingredient | wt. (grams) | Purpose |
| --- | --- | --- |
| Purified water, USP | 78.97 | vehicle |
| Sodium chloride (Morton Salt) | 10.0 | active ingredient |
| Carbopol Ultrez 10 ® (BF Goodrich) | 2.25 | gelling agent |
| 2-Amino-2-methyl-1-propanol (AMP 95 ™, Angus Chemical) | 2.25 | neutralizing agent |
| Polysorbate 20 (Tween 20, ICI Specialities) poly(oxyethylene sorbitan monolaurate | 2.0 | surfactant |
| Cocoamide DEA (Stepan Chemical) | 1.0 | viscosity agent, co-surfactant |
| Benzyl benzoate (Morflex, Inc) | 1.0 | fragrance fixative |
| Anise oil (VWR, Inc.) | 0.5 | active, fragrance |
| Lavender (Bell Flavors & Fragrances) | 0.03 | fragrance |
| Soybean oil (Croda, Inc.) | 2.0 | skin emollient, insect repellent |

The above ingredients are weighed before mixing. The ingredients are added and mixed in standard laboratory equipment in the order that they are listed above. Each ingredient is stirred thoroughly at room temperature before the next ingredient is added. Mixing times for each introduced ingredient is less than one minute per ingredient.

The whole process, from weighing each ingredient to completion, takes about an hour. An overhead mixer is utilized for thorough mixing of each ingredient. The reactions are performed at room temperature, in open air, and in normal room/laboratory lighting The laboratory procedures of Examples 6, 7, and 7a are carried out in a small scale version of the manufacturing equipment described in Examples 1 and 2. Laboratory procedures are designed so that commercial scale-up will not be problematic. More specifically, initially a 100 ml beaker is used. The scale is then enlarged to a 2 liter flask, then enlarged to a 5 gallon drum until finally a pilot plant run using a 100-gallon mixer so that full production may be realized.

Example 7

Laboratory Preparation of a Pediculicidal Gel

| Ingredient | wt. (grams) | Purpose |
| --- | --- | --- |
| Purified water, USP | 22.4 | vehicle |
| Sodium chloride (Morton Salt) | 10.0 | active ingredient |
| Hydroxypropyl methyl cellulose (Methocel ®, Dow Chemical) | 2.25 | gelling agent |
| Purified water, USP | 30.00 | vehicle |
| Polysorbate 20 (Tween 20, ICI) | 2.0 | surfactant |
| Propylene Glycol (Van Waters & Rogers) | 20.0 | humectant |
| Eucalyptus Oil (Berje) | 2.0 | active, fragrance |
| Anise Oil (Chart Corp.) | 4.0 | active, fragrance |
| Lemongrass Oil (Berje) | 4.0 | active, fragrance |
| Vanillin (Rhone-Polenc, Inc.) | 0.5 | fragrance |
| Sodium Metabisulfite (AIC) | 0.1 | antioxidant |

The above ingredients are weighed before mixing. The ingredients are added and mixed in laboratory equipment in the order that they are listed above.

Each ingredient is stirred thoroughly at room temperature before the next ingredient is added. When mixing, stirring is at a rate that will produce a vortex in the mixture

Example 7Ai–v

Laboratory Preparation of Five Pediculicidal Gel Compositions With Varying Opacity Five pediculicidal gels were formulated in the, laboratory and numbered, for 40 comparative purposes, 7Ai–v. These preparations vary in the amount of fragrant oils used. The gels each used the same ingredients that were used in earlier gel formulations, listed below in Table 5, in varying amounts measured in grams. The ingredients were added in the same order as listed below.

TABLE 5

| Composition | 7Ai | 7Aii | 7Aiii | 7Aiv | 7Av |
| --- | --- | --- | --- | --- | --- |
| Water | 82.47 | 82.5 | 82.49 | 82.0 | 82.25 |
| NaCl | 10 | 10 | 10 | 10 | 10 |
| Carbopol ® | 2.25 | 2.25 | 2.25 | 2.25 | 2.25 |
| AMP 95 ™ | 2.25 | 2.25 | 2.25 | 2.25 | 2.25 |
| Tween 20 ™ | 2.0 | 2.0 | 2.0 | 2.0 | 2.0 |
| Ninol ™ | 1.0 | 1.0 | 1.0 | 1.0 | 1.0 |
| Lavender | 0.03 | — | 0.01 | — | — |
| Anise oil | — | — | — | 0.5 | 0.25 |
| Opacity | Clear | Clear | Clear | Opaque | Translucent |

The laboratory formulations of Table 5 were prepared and then tested in vitro on actual live lice. Each of the formulations proved effective in killing the lice. The formulations of Table 5 verify the earlier statement that the clarity or opacity of the gel formulation of the present invention depends upon the amount of oil, which is usually a fragrant oil, that is added. It also demonstrates that the gel may be successfully made without any added fragrance. The active salt ingredient is sufficiently active to eradicate ectoparasites.

Example 8

Laboratory Preparation of a Pediculicidal Detangling Spray Conditioner for Lice-infested Scalp Hair

| Ingredient | wt. (grams) | Purpose |
|---|---|---|
| Purified water, USP | 81.0 | vehicle |
| Hydroxyethyl erucamidopropyl diammionium chloride (Erucyl HE ™, Croda, Inc.) | 3.0 | conditioner |
| Babassuamidopropalkonium chloride (Incroquat BA 85 ™ Croda, Inc.) | 3.0 | conditioner |
| Hydrolyzed collagen (Crotein SPA ™), Croda, Inc | 1.0 | conditioner |
| Dimethizone Co-polyol (Silwet L-7200 ™, Witco) | 0.5 | surfactant |
| Sodium chloride (Morton Salt) | 10.0 | active ingredient |
| Propylene Glycol (Van Waters & Rogers) | 0.5 | humectant |
| Methyl paraben (Protamine Chemicals) | 0.1 | preservative |
| Propyl paraben (Protamine Chemicals) | 0.1 | preservative |
| Benzethonium chloride (Sanko/Lonza) | 0.3 | preservative |
| Lavender (Bell Flavors & Fragrances) | 0.5 | fragrance |

The above ingredients are weighed before mixing. At room temperature, Erucyl HE is added to water. It is stirred until thoroughly dispersed. Incroquat BA 85 is then added and stirred until dispersed. All other ingredients are added separately, mixing thoroughly before adding the next ingredient.

The detangling spray conditioner may be formulated in a solvent system that contains alcohols as well as water. The pediculicidal activity of the detangling spray condition is not dependent on the solvents employed.

Example 9

Laboratory Preparation of a Pediculicidal Shampoo

| Ingredient | wt. (grams) | Purpose |
|---|---|---|
| Purified water, USP | 58.2 | vehicle |
| Sodium lauryl sulfate (Stepan Chemical) | 10.0 | surfactant/foaming agent |
| Tween 20 ™ (ICI) | 2.0 | surfactant |
| Hydrolyzed protein (Croda, Inc) | 1.0 | conditioner |
| Calcium disodium ethylene diamine tetraacetic acid (Riker; BASF) | 0.2 | chelating agent |
| Benzethonium chloride (Lonza) | 0.3 | preservative |
| Cocoamidopropylbetaine (Rhone-Poulenc) | 8.0 | foaming agent, foam booster/stabilizer |
| Cocoamide DEA (Stepan) | 2.0 | viscosity agent, stabilizer, co-surfactant |
| Sodium chloride (Morton) | 10.0 | active ingredient |
| Glycerin Van Waters & Rogers) | 5.0 | humectant |
| Vanillin (Rhone-Poulenc) | 0.3 | fragrance |
| Anise Oil (VWR) | 0.5 | active, fragrance |
| Lavender (Bell) | 0.5 | fragrance |
| Benzyl benzoate (Morflex) | 2.0 | fragrance fixative |

The above ingredients are weighed before mixing. Mix each ingredient separately at room temperature, insuring that each ingredient is thoroughly mixed before adding the next ingredient. The ingredients listed in Table 8 are to be added in the order listed supra; the fragrances are added last.

The formula of Example 8 can also be mixed at elevated temperature, ranging from 60 to 80 degrees F. The higher temperatures accelerate the production of the formulations.

For comparative purposes, the data presented in Examples 4 and 5 above indicate that the natural composition of this invention performs at least as well as a widely-used prior art chemical product for pediculicidal activity. It is shown that both adult lice and nits are killed by the non-toxic, natural composition of this invention.

According to their packaging, anti-lice preparations that contain the chemical permethrin as the active ingredient may cause sensitivity to eyes and mucous membranes, may cause breathing difficulty or asthma in susceptible persons. Packaging for such chemical lice treatments lists warnings regarding use by pregnant women. The packaging for the kit containing a gel pediculicide of the instant invention has no such warning.

Scope of the Invention

The above presents a description of the best mode contemplated of carrying out the present invention, and of the manner and process of making and using it, in such full, clear, concise, and exact terms as to enable any person skilled in the art to which it pertains to make and use this invention. This invention is, however, susceptible to modifications and alternate constructions from that discussed above which are fully equivalent. Consequently, it is not the intention to limit this invention to the particular embodiments disclosed. On the contrary, the intention is to cover all modifications and alternate constructions coming within the spirit and scope of the invention as generally expressed by the following claims, which particularly point out and distinctly claim the subject matter of the invention.

What is claimed is:

1. A pediculicidal gel composition that eliminates lice and nits from the scalp of an infested person comprising
   at least 10 weight percent of an alkali-metal halide salt;
   from about 2 to about 5 weight percent of a carboxyvinyl polymer gelling agent;
   from about 2 to about 5 weight percent of 2-amino-2-methyl-1-propanol as a neutralizing agent;
   from about 2 to about 5 weight percent of a surfactant;
   about one weight percent of a co-surfactant;
   from 0.0 to about 0.5 weight percent of anise oil plant essence; and
   the balance purified water which composition is translucent and non-toxic to the person to whose scalp it is applied.

2. The pediculicidal gel composition of claim 1 wherein the salt is sodium chloride.

3. The pediculicidal gel composition of claim 1 whose viscosity ranges from at least 6,000 cps to about 14,000 cps.

4. The pediculicidal gel composition of claim 1 wherein the surfactant is poly(oxyethylene sorbitan monolaurate).

5. The pediculicidal gel composition of claim 1 wherein the co-surfactant is cocoamide DEA.

6. The pediculicidal gel composition of claim 1 which contains at least 0.5 weight percent of anise oil plant essence and is an opaque white gel.

7. The pediculicidal gel composition of claim 1 which contains about 0.25 weight percent of anise oil plant essence and is translucent.

8. The pediculicidal gel composition of claim 1 which contains from 0.0 to less than 0.25 weight percent lavender and is clear.

9. A pediculicidal lotion composition that has a viscosity of from 100 to 10,000 cps and comprises from 10 to 20 weight percent of sodium chloride;

from 0.5 to 30 weight percent of hykdroxyethyl cellulose carboxyvinyl polymer gelling agent;

from 0.1 to 3 weight percent of cocoamide DEA gel promoter;

from 0.5 to 5 weight percent of anise oil plant essence;

from about 2 to about 5 weight percent of 2-amino-2-methyl-1-propanol neutralizing agent;

from about 2 to about 5 weight percent of isopropyl myristate skin emollient;

from about 2 to about 5 weight percent of sorbitan monolaurate surfactant; and the remainder purified water which composition is non-toxic to person applying it.

10. A pediculicidal shampoo composition with a viscosity of from about 350 to 15,000 cps comprising a) about 10 weight percent of sodium chloride salt;

b) about 12 weight percent of poly(oxyethylene sorbitan monolaurate surfactant/foaming agent;

c) about 1 weight percent of a hydrolyzed protein conditioner;

d) about 20 weight percent of a combination of performance additives including foaming agent sodium lauryl sulfate, viscosity agent cocoamide DEA: chelating agent calcium disodium EDTA, preservative benzethonium chloride, humectant, glycerin, fragrances vanillin, anise oil, and lavender, fragrance fixative benzyl benzoate and the remainder is purified water which composition is non-toxic to a person using it.

11. A pediculicidal detangling, spray conditioner for hair with a viscosity of from about 100 to about 1,000 cps comprising a) from 10 to 20 weight percent of sodium chloride;

b) from 0.5 to 5 weight percent of lavender;

c) from 0.5 to 5 weight percent of a mixture of babassuamidopropalkonium chloride, hydrolyzed collagen, and hydroxyethyl erucamidopropyl diammonium chloride;

d) from 0.5 to 10 weight percent of dimetihizone co-polyol;

e) up to about 1 weight percent of a humectant;

f) up to about 1 weight percent of a mixture of methyl paraben, propyl paraben, and benzethonium chloride; and the remainder purified water.

12. A method for eradicating lice and nits from the hair of a host organism comprising contacting the infested area topically with the gel composition of claim 1, that is non-toxic to the host organism and stable for a time period of at least three years.

* * * * *

UNITED STATES PATENT AND TRADEMARK OFFICE
CERTIFICATE OF CORRECTION

PATENT NO. : 6,607,716 B1  Page 1 of 1
DATED : August 19, 2003
INVENTOR(S) : Smith, R.L. et al.

It is certified that error appears in the above-identified patent and that said Letters Patent is hereby corrected as shown below:

<u>Title page,</u>
Item [73], Assignee, the Assignee name is misspelled and should read -- Tec Labs, Inc. --

<u>Column 2,</u>
Line 29, delete comma typed after the word "to".

<u>Column 6,</u>
Line 10, please change "is may be" to -- is --.

<u>Column 11,</u>
Line 17, delete comma and extra space after the word "is".

Signed and Sealed this

Twenty-fifth Day of November, 2003

JAMES E. ROGAN
*Director of the United States Patent and Trademark Office*